United States Patent [19]

Harley et al.

[11] Patent Number: 4,935,565

[45] Date of Patent: Jun. 19, 1990

[54] PROCESS AND CATALYST FOR HYDROCHLORINATION OF HYDROCARBONS

[75] Inventors: A. Dale Harley, Midland, Mich.; Michael T. Holbrook, Baton Rouge, La.

[73] Assignee: The Dow Chemical Company, Midland, Mich.

[21] Appl. No.: 235,579

[22] Filed: Aug. 24, 1988

[51] Int. Cl.$^5$ .............................. C07C 17/16
[52] U.S. Cl. ................... 570/258; 570/195; 570/201
[58] Field of Search ................ 570/258, 195, 201

[56] References Cited

U.S. PATENT DOCUMENTS

| | | |
|---|---|---|
| 53,925 | 5/1887 | Harley . |
| 2,497,150 | 2/1950 | Carlson et al. ............ 260/657 |
| 4,073,816 | 2/1978 | Herrmann ............ 260/648 R |

FOREIGN PATENT DOCUMENTS

| | | |
|---|---|---|
| 3332253A1 | 7/1983 | Fed. Rep. of Germany . |
| 213782 | 3/1968 | U.S.S.R. . |

OTHER PUBLICATIONS

Wolfgang Sundermeyer, Ber. 97(4) 1069–74 (1964) C.A. abstract only.
M. I. Levinsku et al., Izobret. Prom. Obraztsy, Tovarnye Znaks 1968, 45(11) 18, C.A. Abstract only.
Derwent 86-285035/44.
Derwent 66318S-E.
Derwent 00102T-E.
Derwent 5711x/30.

*Primary Examiner*—Howard T. Mars
*Attorney, Agent, or Firm*—Paula Sanders Ruhr

[57] ABSTRACT

Methyl chloride is produced by contacting methanol and hydrogen chloride in the vapor phase in the presence of $KZnCl_3$ supported on silica. The process produces methyl chloride in good yield with minimal formation of dimethyl ether as a by-product.

17 Claims, No Drawings

PROCESS AND CATALYST FOR HYDROCHLORINATION OF HYDROCARBONS

BACKGROUND OF THE INVENTION

This invention relates to catalytic hydrochlorination processes. In particular, the invention relates to the catalytic hydrochlorination of hydrocarbyl compounds.

Chlorinated hydrocarbons have various utilities as industrial chemicals and solvents. For example, methyl chloride is useful as a catalyst carrier in low temperature polymerizations as a fluid for thermometric and thermostatic equipment: as a methylating agent in organic synthesis, such as of methylcellulose: in the preparation of silicone rubbers; and as an extractant and low temperature solvent.

Methods for the production of chlorinated hydrocarbons, such as methyl chloride, are well-known. In a typical method for the production of methyl chloride, vaporized methanol and hydrogen chloride are mixed in approximately equimolar proportions and passed through a converter packed with a catalyst such as alumina gel or zinc chloride on activated carbon to form methyl chloride. Other known methods involve reactions in the liquid phase using an aqueous solution of catalyst. For example, U.S. Pat. No. 4,073,816 teaches that monochloroalkanes or monochlorocycloalkanes can be prepared by reacting an alcohol with hydrogen chloride in the presence of aqueous zinc chloride. German Offensive 3332253 teaches that mixtures containing alcohols and ethers may be converted to alkyl halides by reactions with hydrogen chloride in the presence of an aluminum-zinc chloride catalyst. This reference further teaches that small amounts of alkali metal chlorides and larger amounts of cadmium, iron and/or magnesium chlorides may be added with the zinc chloride to increase the efficiency of the catalyst.

Such methods do not resolve all the existing problems. The problems relating to the manufacture of chlorinated hydrocarbons include excessive production of by-products: requirements for use of excess hydrochloric acid and excessive coking of the catalyst. An additional problem related to the use of alumina or alumina supported catalysts is the breakdown of the alumina to produce bohemite. What is needed is a non-alumina catalyst which results in a high yield of chlorinated hydrocarbon: which permits the complete conversion of hydrochloric acid; which does not experience excessive coke formation: and which reduces the amount of by-products formed.

SUMMARY OF THE INVENTION

In one aspect, the present invention is such a hydrochlorination catalyst comprising a Group IA cation, ion, a Group IIA or IIB cation and a neutralizing number of counter anions supported on a non-alumina porous carrier. The molar ratio of the Group IA cation to the Group IIA or IIB cation is at least about 0.5:1 and no greater than about 1.5:1.

In a second aspect, the present invention is a process for the hydrochlorination of hydrocarbyl compounds to form chlorinated hydrocarbyl compounds wherein the hydrocarbyl compounds and hydrogen chloride are contacted in the vapor phase in the presence of the catalyst described above under reaction conditions sufficient to form the chlorinated hydrocarbyl compounds.

The chlorinated hydrocarbyl compounds produced by the practice have various utilities as industrial chemicals and solvents. Methyl chloride, for example, is useful as a catalyst carrier in low temperature polymerizations: as a fluid for thermometric and thermostatic equipment: as a methylating agent in organic synthesis, such as of methylcellulose; and as an extractant and low temperature solvent.

It is surprising that the use of a catalyst supported on a non-alumina support and comprising the specified molar ratio of the cations described above results in a high yield of chlorinated hydrocarbyl compounds with reduced formation of by-products and with minimal coking of the catalyst. The use of the specified non-alumina supported catalyst eliminates the problem of bohemite formation while maintaining high yields.

DETAILED DESCRIPTION OF THE INVENTION

The catalyst of the present invention is advantageously a salt of a Group IA metal (alkali metal): a Group IIA or IIB, preferably Group IIB, metal: and a neutralizing number of counter anions supported on a non-alumina porous carrier material. Preferred Group IA metals include sodium, potassium, rubidium, lithium and cesium, with potassium and cesium being more preferred and potassium being most preferred. The preferred Group IIB metals include zinc, cadmium and mercury with zinc being more preferred. While any counter anion, such as bromide, chloride and fluoride, is suitable in the catalyst of this invention, the halides are preferred with chloride being most preferred. Other suitable anions are nitrates, sulfate, phosphate, acetates, oxylate and cyanides.

The molar ratio of Group IA metal to Group IIA or IIB metal in the salt is preferably at least about 0.5:1 and no greater than about 1.5:1. It is more preferred that the molar ratio is at least about 0.9:1 and no greater than about 1.1:1 and most preferred that approximately equimolar portions of the two metals are used. The amount of counter anion used is that which is sufficient to neutralize the cations of the salt.

Any non-alumina support which will withstand the hydrochlorination conditions described herein can be used in the process of the present invention. Examples of appropriate supports include the well-known carbon supports such as activated carbon, carbon black, chars and coke. Other suitable supports that may be used to support the catalyst include pumice, silica gel, asbestos, diatomaceous earth, fullers earth, titania, zirconia, magnesia, magnesium silicate, silicon carbide, silicalite, and silica. A preferred support is silica. A silica having a surface area between 100 m$^2$/g and 300 m$^2$/g and a pore volume in the range of 0.75 cc/ to 1.4 cc/g is particularly active in the process of this invention.

The salt is suitably supported on the carrier material by any standard impregnation technique such as that disclosed in *Experimental Methods in Catalytic Research*, Vol. II, edited by R. B. Anderson and P. T. Dawson, Academic Press, New York, 1978. A solution of both the Group IA and Group IIA or IIB metal cations and the associated anions may be employed to impregnate the support material or the metal salts may be impregnated from separate solutions. The resulting catalyst comprising the catalytically active salt and the support preferably comprises from about 1 to about 50 weight percent of the Group IIA or IIB metal salt, e.g., $ZnCl_2$, and from about 0.5 to about 30 weight percent of the Group IA metal salt, e.g., KCl, based on the percentage by weight of the total salts to the support. It is preferred to use at least about 20 and no greater than about 30 weight percent of the Group IIA or IIB metal salt and at least about 10 and no greater than about 20 weight percent of the Group IA metal salt and more preferred to use about 20 weight percent of the Group IIA or IIB metal salt and about 10 weight percent of the Group IIA metal salt. Preferred weight percents of the two salts are selected so as to result in approximately equimolar proportions of the Group IA and Group IIA or IIB salt being used.

The process of the present invention comprises contacting a alcohol and hydrogen chloride in the presence of the aforementioned catalyst under reaction conditions sufficient to produce the corresponding chlorinated hydrocarbon. Examples of alcohols useful in the practice of this invention include compounds corresponding to the formula

ROH wherein R is alkyl, aryl, arylalkyl and alkylaryl. It is preferred that R is alkyl and more preferred that R is lower alkyl having from about 1 to about 5 carbon atoms. It is most preferred that R is alkyl having from 1 to about 3 carbon atoms. Examples of preferred alcohol compounds thus include methanol, ethanol and propanol with methanol being more preferred.

Molar ratios of alcohol to hydrogen chloride useful in the practice of this invention are generally at least about 1:10 and no greater than about 10:1. When hydrogen chloride is used in excess, it is preferred that the amount of excess hydrogen chloride is no more than about 30 molar percent. It is preferred that the alcohol be used in excess. When the alcohol is used in excess, it is preferred that the molar ratio of alcohol to hydrogen chloride is about no greater than about 2:1 and more preferred that it is no greater than about 1.5:1 and most preferred that is is about 1.1:1.

The temperature range useful in the practice of this invention is any at which the hydrochlorination reaction will proceed. Preferably, the reaction is conducted at a temperature of at least about 25° C. and no greater than about 475° C. with at least about 175° C. to no greater than about 300° C. being more preferred. The most preferred temperature ranges from at least about 250° C. to no greater than about 275° C. Pressures typically employed in the process of the present invention are at least about 14 psig and no greater than about 500 psig. Preferred pressures are at least about 35 psig and no greater than about 150 psig.

Gas hourly space velocities are suitably at least about 100 and no greater than about 10,000 hours$^{-1}$, preferably at least about 300 and no greater than about 3000 h$^{-1}$.

The process may be operated in a batch mode or continuously although continuous operation is preferred. In a preferred embodiment, vaporized methanol and hydrogen chloride are added in approximately equimolar proportions to a fixed bed reactor containing a KZnCl$_3$ catalyst supported on silica. The resultant products are separated by distillation.

The process of this invention is effective in reducing the amount of by-products formed. In a preferred embodiment wherein methanol and hydrogen chloride react to form methyl chloride, the production of by-products such as dimethyl ether is decreased. The process of the present invention also results in a long-lived catalyst. The catalyst of the present invention is stable and the absence of alumina eliminates the problem of bohemite formation.

ILLUSTRATIVE EMBODIMENTS

The following examples are provided to illustrate the invention and should not be interpreted as limiting it in any way. Unless stated otherwise, all parts and percentages are by weight.

EXAMPLE 1 —CATALYST PREPARATION

A silica sample is sieved between three screens and the fractions retained by 4 mesh, 5 mesh and 8 mesh, respectively, are collected. The 8 mesh fraction is used in the preparation of 200 g samples of about 500 cubic centimeters each. A 200 g sample is placed in a 2 liter dish and dried 48 hours at 150° C. The sample is transferred to 1 liter fluted flask, placed on a rotovap and cooled to 70° C. under vacuum. The silica is then impregnated with a solution of 60 g of ZnCl$_2$ and 32.81 g of KCl in a total volume of 278 cubic centimeters of water. The impregnated catalyst is returned to the 2 liter dish and air dried for 24 hours and then dried for an additional 25 hours at 150° C.

EXAMPLE 2

A three-liter portion of catalyst, prepared as described above, is placed into an Inconel reactor that is 20 feet long and 1.25 inches in diameter. The reactor is then purged with nitrogen for 48 hours at 220° C. The catalyst is then conditioned with HCl mixed with nitrogen prior to reaction with methanol. The proportions of methanol to hydrogen chloride and the reaction temperature are varied as shown in Table I below. The reactor effluent is analyzed by gas chromatography to determine the conversion obtained and the amount of dimethyl ether produced relative to the amount of methyl chloride produced. The results obtained are shown in Table I below.

TABLE I

| Run | Methanol (lb/hr) | HCl (lb/hr) | Temp (°C.) | Conversion [1] (%) | DME/MC [2] (ppm) |
|---|---|---|---|---|---|
| 1 | 8.00 | 10.00 | 220 | 96.6 | 11726 |
| 2 | 8.00 | 10.00 | 235 | 96.4 | 11545 |
| 3 | 3.92 | 5.57 | 220 | 99.0 | 6981 |
| 4 | 3.92 | 4.91 | 220 | 98.2 | 8957 |
| 5 | 7.46 | 10.57 | 220 | 98.4 | 7713 |
| 6 | 5.83 | 7.78 | 220 | 98.4 | 8161 |
| 7 | 8.00 | 10.00 | 220 | 93.1 | 13780 |
| 8 | 4.14 | 4.95 | 220 | 94.3 | 13441 |
| 9 | 8.00 | 10.00 | 220 | 93.4 | 14065 |
| 10 | 4.24 | 4.84 | 220 | 91.3 | 16209 |
| 11 | 9.81 | 10.34 | 220 | 93.6 | 13900 |

[1] Conversion of methanol to methyl chloride
[2] Parts of dimethyl ether produced per million parts of methyl chloride The data above illustrate that the use of the catalytic process of this invention results in a high rate of conversion of methanol. Runs 1 and 2 demonstrate that an increase in the reaction temperature from 220° C. to 235° C. has little effect on conversion or dimethyl ether production. Runs 3 and 4 demonstrate the effect of varying the ratio of methanol to hydrogen chloride. Run 3 represents a 25 percent molar excess of hydrogen chloride while Run 4 shows a 10 percent molar excess. At the 10 percent excess level, the conversion decreases and the dimethyl ether production increases although in either case the conversion is high and the dimethyl ether production is low. Runs 8, 10 and 11 show the effect of decreasing the molar proportion of HCl until methanol is used in excess. The ratios of methanol to HCl change from 1:1.05 in Run 8 to 1:1 in Run 10 and to 1.13:1 and follow the trend shown in Runs 3 and 4. These trends indicate that high conversion and acceptably low dimethyl ether production may be obtained when methanol is used in excess. Runs 1, 7 and 9 are all identical and demonstrate that after a breaking in period, the catalyst is stable within the time frame of the experiment.

What is claimed is:

1. A process for the hydrochlorination of alkanols corresponding to the formula

ROH wherein R is alkyl, to form chlorinated compounds comprising contacting the alkanol and hydrogen chloride at a molar ratio of at least about 1:10 and no greater than about 10:1 in the vapor phase in the presence of a hydrochlorination catalyst, said catalyst comprising a first cation selected from the group consisting of potassium, cesium, sodium, rubidium and lithium and a second cation selected from the group consisting of zinc, cadmium and mercury in a molar ratio of first cation to second cation of at least about 0.5:1 and no greater than about 1.5:1 and a neutralizing number of counter anions supported on a non-alumina porous carrier under reaction conditions sufficient to form the chlorinated compounds corresponding to the starting alkanols.

2. The process of claim 1 wherein the alkanol is a lower alkanol.

3. The process of claim 1 wherein the lower alkanol is methanol.

4. The process of claim 3 wherein the molar ratio of methanol to hydrogen chloride is at least about 1.1:1 and no greater than about 2:1.

5. The process of claim 4 wherein the molar ratio of methanol to hydrogen chloride is at least about 1.1:1 and no greater than about 1.5:1.

6. The process of claim 1 wherein the reaction temperature is at least about 175° C. and no greater than about 300° C.

7. The process of claim 6 wherein the reaction temperature is at least about 250° C. and no greater than about 275° C.

8. The process of claim 1 wherein the reaction pressure is at least about 35 psig and no greater than about 150 psig.

9. The process of claim 10 wherein the first cation of the catalyst is a cation of a metal selected from the group consisting of potassium and cesium.

10. The process of claim 26 wherein the second cation of the catalyst is a zinc cation.

11. The process of claim 10 wherein the counter ion of the catalyst is chloride.

12. The process of claim 11 wherein the ratio of potassium to zinc is at least about 0.9:1 and no greater than about 1.1:1.

13. The process of claim 12 wherein the ratio of potassium to zinc is about 1:1.

14. The process of claim 13 wherein the catalyst is KCl and $ZnCl_2$ supported on silica having a surface area between 100 $m^2/g$ and 300 $m^2/g$ and a pore volume in the range of 0.75 of 0.75 cc/g to 1.4 cc/g.

15. The process of claim 14 wherein methanol and hydrogen chloride are contacted in the vapor phase at a temperature of about 250° C. in the presence of a catalyst comprising KCl and $ZnCl_2$ supported on silica under reaction conditions sufficient to produce methyl chloride.

16. The process of claim 9 wherein the first cation of the catalyst is potassium.

17. The process of claim 3 wherein the molar ratio of methanol to hydrogen chloride ranges from 1.131 to 1:1.05.

* * * * *

UNITED STATES PATENT AND TRADEMARK OFFICE
CERTIFICATE OF CORRECTION

PATENT NO. : 4,935,565

DATED : June 19, 1990

INVENTOR(S) : A. Dale Harley and Michael T. Holbrook

It is certified that error appears in the above-identified patent and that said Letters Patent is hereby corrected as shown below:

On the first page under OTHER PUBLICATIONS, "Derwent 5711x/30" should correctly read -- Derwent 57111x/30 --.

Column 1, line 12, "polymerizations" should correctly read -- polymerizations; --.

Column 1, line 13, "equipment:" should correctly read -- equipment; --.

Column 1, line 14, "methylcellulose:" should correctly read -- methylcellulose; --.

Column 1, line 41, "by-products:" should correctly read -- by-products; --.

Column 1, line 47, "hydrocarbon:" should correctly read -- hydrocarbon; --.

Column 1, line 49, "formation:" should correctly read -- formation; --.

Column 2, line 3, "polymerizations:" should correctly read -- polymerizations; --.

Column 2, line 4, "equipment:" should correctly read -- equipment; --.

Column 2, line 19, "(alkali metal):" should correctly read -- (alkali metal); --.

UNITED STATES PATENT AND TRADEMARK OFFICE
CERTIFICATE OF CORRECTION

PATENT NO. : 4,935,565

DATED : June 19, 1990

INVENTOR(S) : A. Dale Harley and Michael T. Holbrook

It is certified that error appears in the above-identified patent and that said Letters Patent is hereby corrected as shown below:

Column 2, line 20, "metal:" should correctly read -- metal; --.

Column 2, line 53, "0.75 cc/" should correctly read -- 0.75 cc/g --.

Column 5, line 36, "claim 1" should correctly read -- claim 2 --.

Column 6, line 13, "claim 10" should correctly read -- claim 1 --.

Column 6, line 16, "claim 26" should correctly read -- claim 9 --.

Column 6, line 28, "of 0.75" should correctly read -- [of 0.75] --.

Column 6, line 48, "1.131" should correctly read -- 1.13:1 --.

Signed and Sealed this

Thirty-first Day of December, 1991

Attest:

HARRY F. MANBECK, JR.

*Attesting Officer*   *Commissioner of Patents and Trademarks*